(12) United States Patent
Sode et al.

(10) Patent No.: US 7,244,600 B2
(45) Date of Patent: Jul. 17, 2007

(54) GLUCOSE DEHYDROGENASE

(75) Inventors: Koji Sode, Tokyo (JP); Satoshi Igarashi, Tokyo (JP)

(73) Assignee: Ultizyme International Ltd., Tokyo (JP)

( * ) Notice: Subject to any disclaimer, the term of this patent is extended or adjusted under 35 U.S.C. 154(b) by 449 days.

(21) Appl. No.: 10/471,552

(22) PCT Filed: Mar. 7, 2002

(86) PCT No.: PCT/JP02/02124

§ 371 (c)(1),
(2), (4) Date: Dec. 11, 2003

(87) PCT Pub. No.: WO02/072839

PCT Pub. Date: Sep. 19, 2002

(65) Prior Publication Data

US 2004/0191883 A1      Sep. 30, 2004

(30) Foreign Application Priority Data

Mar. 13, 2001 (JP) ............................. 2001-070413

(51) Int. Cl.
| | |
|---|---|
| C12N 9/04 | (2006.01) |
| C12N 15/00 | (2006.01) |
| C12N 1/20 | (2006.01) |
| C12Q 1/00 | (2006.01) |
| C12Q 21/04 | (2006.01) |
| C12M 1/00 | (2006.01) |
| C07H 21/04 | (2006.01) |
| C12Q 1/68 | (2006.01) |

(52) U.S. Cl. ............... 435/190; 435/440; 435/4; 435/6; 435/252.3; 435/320.1; 435/69.1; 435/71.1; 536/23.2; 536/23.7; 204/403.04; 204/403.11

(58) Field of Classification Search ............ 435/190, 435/440, 252.3, 320.1, 4, 6, 18, 25, 69.1, 435/71.1; 536/23.2, 23.7
See application file for complete search history.

(56) References Cited

U.S. PATENT DOCUMENTS 4,908,773 A * 3/1990 Pantoliano et al. .......... 702/138
2006/0099698 A1 * 5/2006 Sode ........................... 435/189

FOREIGN PATENT DOCUMENTS

JP    10-243786 A    9/1998

OTHER PUBLICATIONS

Sode et al. Biotechnology Letters 21: 707-710, 1999.*
Cleton-Jensen et al.—cloned sequence.*
Igarashi et al., Biochem. Biophys. Res. Comm., vol. 264, No. 3, pp. 820-824 (1999).
Velanker et al., Protein Science, vol. 8, pp. 930-933 (1990).
Mansfeld et al., J. Biol. Chem., vol. 272, No. 17, pp. 11152-11156 (1997).

(Continued)

Primary Examiner—P. Achutamurthy
Assistant Examiner—Ying D. Pak
(74) Attorney, Agent, or Firm—Birch, Stewart, Kolasch & Birch, LLP (57) ABSTRACT

Disclosed is a water-soluble PQQGDH wherein two subunits are linked together via a disulfide bond. The water-soluble PQQGDH of the invention exhibits improved thermal stability.

8 Claims, 5 Drawing Sheets

OTHER PUBLICATIONS

Oubrie et al., J. Mol. Biol., vol. 289, pp. 319-333 (1999).
Oubrie et al., The EMBO Journal, vol. 18, No. 19, pp. 5187-5194 (1999).
K. Matsushita et al., Biosci. Biotech. Biochem., 59 (8), 1548-1555, 1995.
A. Cleton-Jansen et al., Mol. Gen Genet (1989) 217: 430-436.
Yoshida, Hiromi et al.; Protein Engineering, vol. 12, No. 1, pp. 63-70 (1999).

* cited by examiner

SEQUENCE LISTING

<160> NUMBER OF SEQ ID NOS: 13

<210> SEQ ID NO 1
<211> LENGTH: 454
<212> TYPE: PRT
<213> ORGANISM: Acinetobacter calcoaceticus

<400> SEQUENCE: 1

```
Asp Val Pro Leu Thr Pro Ser Gln Phe Ala Lys Ala Lys Ser Glu Asn
 1               5                  10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
    50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ser Thr Asp Thr Leu
        115                 120                 125

Glu Lys Pro Val Asp Leu Leu Ala Gly Leu Pro Ser Ser Lys Asp His
    130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
```

```
                    165                 170                 175
Gln Ala Gln His Thr Pro Thr Gln Gln Glu Leu Asn Gly Lys Asp Tyr
            180                 185                 190
His Thr Tyr Met Gly Lys Val Leu Arg Leu Asn Leu Asp Gly Ser Ile
        195                 200                 205
Pro Lys Asp Asn Pro Ser Phe Asn Gly Val Val Ser His Ile Tyr Thr
    210                 215                 220
Leu Gly His Arg Asn Pro Gln Gly Leu Ala Phe Thr Pro Asn Gly Lys
225                 230                 235                 240
Leu Leu Gln Ser Glu Gln Gly Pro Asn Ser Asp Asp Glu Ile Asn Leu
                245                 250                 255
Ile Val Lys Gly Gly Asn Tyr Gly Trp Pro Asn Val Ala Gly Tyr Lys
            260                 265                 270
Asp Asp Ser Gly Tyr Ala Tyr Ala Asn Tyr Ser Ala Ala Ala Asn Lys
        275                 280                 285
Ser Ile Lys Asp Leu Ala Gln Asn Gly Val Lys Val Ala Ala Gly Val
    290                 295                 300
Pro Val Thr Lys Glu Ser Glu Trp Thr Gly Lys Asn Phe Val Pro Pro
305                 310                 315                 320
Leu Lys Thr Leu Tyr Thr Val Gln Asp Thr Tyr Asn Tyr Asn Asp Pro
                325                 330                 335
Thr Cys Gly Glu Met Thr Tyr Ile Cys Trp Pro Thr Val Ala Pro Ser
            340                 345                 350
Ser Ala Tyr Val Tyr Lys Gly Gly Lys Lys Ala Ile Thr Gly Trp Glu
        355                 360                 365
Asn Thr Leu Leu Val Pro Ser Leu Lys Arg Gly Val Ile Phe Arg Ile
    370                 375                 380
Lys Leu Asp Pro Thr Tyr Ser Thr Thr Tyr Asp Asp Ala Val Pro Met
385                 390                 395                 400
Phe Lys Ser Asn Asn Arg Tyr Arg Asp Val Ile Ala Ser Pro Asp Gly
                405                 410                 415
Asn Val Leu Tyr Val Leu Thr Asp Thr Ala Gly Asn Val Gln Lys Asp
            420                 425                 430
Asp Gly Ser Val Thr Asn Thr Leu Glu Asn Pro Gly Ser Leu Ile Lys
        435                 440                 445
Phe Thr Tyr Lys Ala Lys
    450

<210> SEQ ID NO 2
<211> LENGTH: 1612
<212> TYPE: DNA
<213> ORGANISM: Acinetobacter calcoaceticus

<400> SEQUENCE: 2
agctactttt atgcaacaga gcctttcaga aatttagatt ttaatagatt cgttattcat      60
cataatacaa atcatataga gaactcgtac aaacccttta ttagaggttt aaaaattctc     120
ggaaattttt gacaatttat aaggtggaca catgaataaa catttattgg ctaaaattgc     180
tttattaagc gctgttcagc tagttacact ctcagcattt gctgatgttc ctctaactcc     240
atctcaattt gctaaagcga aatcagagaa ctttgacaag aaagttattc tatctaatct     300
aaataagccg catgctttgt tatggggacc agataatcaa atttggttaa ctgagcgagc     360
aacaggtaag attctaagag ttaatccaga gtcgggtagt gtaaaaacag tttttcaggt     420
accagagatt gtcaatgatg ctgatgggca gaatggttta ttaggttttg ccttccatcc     480
```

```
tgattttaaa aataatcctt atatctatat ttcaggtaca tttaaaaatc cgaaatctac    540
agataaagaa ttaccgaacc aaacgattat tcgtcgttat acctataata aatcaacaga    600
tacgctcgag aagccagtcg atttattagc aggattacct tcatcaaaag accatcagtc    660
aggtcgtctt gtcattgggc cagatcaaaa gatttattat acgattggtg accaagggcg    720
taaccagctt gcttatttgt tcttgccaaa tcaagcacaa catacgccaa ctcaacaaga    780
actgaatggt aaagactatc acacctatat gggtaaagta ctacgcttaa atcttgatgg    840
aagtattcca aaggataatc caagttttaa cggggtggtt agccatattt atacacttgg    900
acatcgtaat ccgcagggct tagcattcac tccaaatggt aaattattgc agtctgaaca    960
aggcccaaac tctgacgatg aaattaacct cattgtcaaa ggtggcaatt atggttggcc   1020
gaatgtagca ggttataaag atgatagtgg ctatgcttat gcaaattatt cagcagcagc   1080
caataagtca attaaggatt tagctcaaaa tggagtaaaa gtagccgcag ggtccctgt    1140 gacgaaagaa tctgaatgga ctggtaaaaa ctttgtccca ccattaaaaa ctttatatac   1200
cgttcaagat acctcaaact ataacgatcc aacttgtgga gagatgacct acatttgctg   1260
gccaacagtt gcaccgtcat ctgcctatgt ctataagggc ggtaaaaaag caattactgg   1320
ttgggaaaat acattattgg ttccatcttt aaaacgtggt gtcattttcc gtattaagtt   1380
agatccaact tatagcacta cttatgatga cgctgtaccg atgtttaaga gcaacaaccg   1440
ttatcgtgat gtgattgcaa gtccagatgg gaatgtctta tatgtattaa ctgatactgc   1500
cggaaatgtc caaaagatg atggctcagt aacaaataca ttagaaaacc caggatctct    1560
cattaagttc acctataagg ctaagtaata cagtcgcatt aaaaaaccga tc            1612

<210> SEQ ID NO 3
<211> LENGTH: 7
<212> TYPE: PRT
<213> ORGANISM: Acinetobacter calcoaceticus

<400> SEQUENCE: 3

Pro Thr Tyr Cys Thr Thr Tyr
 1               5

<210> SEQ ID NO 4
<211> LENGTH: 7
<212> TYPE: PRT
<213> ORGANISM: Acinetobacter calcoaceticus

<400> SEQUENCE: 4

Pro Thr Cys Ser Thr Thr Tyr
 1               5

<210> SEQ ID NO 5
<211> LENGTH: 28
<212> TYPE: DNA
<213> ORGANISM: Artificial Sequence
<220> FEATURE:
<223> OTHER INFORMATION: primer for point mutation

<400> SEQUENCE: 5
catcataagt agtgcaataa gttggatc                                        28

<210> SEQ ID NO 6
<211> LENGTH: 32
<212> TYPE: DNA
<213> ORGANISM: Artificial Sequence
<220> FEATURE:
```

<223> OTHER INFORMATION: primer for point mutation

<400> SEQUENCE: 6
catcataagt agtgcaacaa gttggatcta ac                      32

<210> SEQ ID NO 7
<211> LENGTH: 24
<212> TYPE: DNA
<213> ORGANISM: Artificial Sequence
<220> FEATURE:
<223> OTHER INFORMATION: primer for point mutation

<400> SEQUENCE: 7
aggtgatgat ttctcatgct gtga                               24

<210> SEQ ID NO 8
<211> LENGTH: 30
<212> TYPE: DNA
<213> ORGANISM: Artificial Sequence
<220> FEATURE:
<223> OTHER INFORMATION: primer for point mutation

<400> SEQUENCE: 8
cctttggaat ttttccatca agatttaagc                         30

<210> SEQ ID NO 9
<211> LENGTH: 7
<212> TYPE: PRT
<213> ORGANISM: Acinetobacter calcoaceticus

<400> SEQUENCE: 9

Thr Gly Lys Asn Phe Val Pro
 1               5

<210> SEQ ID NO 10
<211> LENGTH: 7
<212> TYPE: PRT
<213> ORGANISM: Acinetobacter calcoaceticus

<400> SEQUENCE: 10

Ser Thr Thr Tyr Asp Asp Ala
 1               5

<210> SEQ ID NO 11
<211> LENGTH: 22
<212> TYPE: DNA
<213> ORGANISM: Artificial Sequence
<220> FEATURE:
<223> OTHER INFORMATION: primer for point mutation

<400> SEQUENCE: 11
gggacaaagc atttaccagt cc                                 22

<210> SEQ ID NO 12
<211> LENGTH: 29
<212> TYPE: DNA
<213> ORGANISM: Artificial Sequence
<220> FEATURE:
<223> OTHER INFORMATION: primer for point mutation

<400> SEQUENCE: 12
catcggtaca gcgtcatcac aagtagtgc                          29

<210> SEQ ID NO 13
<211> LENGTH: 7

```
<212> TYPE: PRT
<213> ORGANISM: Acinetobacter calcoaceticus

<400> SEQUENCE: 13

Pro Thr Cys Cys Thr Thr Tyr
 1               5
```

GLUCOSE DEHYDROGENASE

This application is the national phase under 35 U.S.C. § 371 of PCT International Application No. PCT/JP02/02124 which has an International filing date of Mar. 7, 2002, which designated the United States of America.

TECHNICAL FIELD

The present invention relates to the preparation of glucose dehydrogenases having pyrrolo-quinoline quinone as a coenzyme (PQQGDH) and their use for glucose assays.

BACKGROUND ART

Blood glucose is an important marker for diabetes. In the fermentative production using microorganisms, glucose levels are assayed for monitoring the process. Conventional glucose assays were based on enzymatic methods using glucose oxidase (GOD) or glucose-6-phosphate dehydrogenase (G6PDH). However, GOD-based assays require addition of catalase or peroxidase to the assay system in order to quantitate the hydrogen peroxide generated by glucose oxidation reaction. G6PDHs have been used for spectrophotometric glucose assays, in which case a coenzyme NAD(P) must be added to the reaction system.

Recently, PQQGDH is used as a new enzyme in place of GOD or G6PDH, which have been conveniently used for enzymatic assay of glucose (see, JP A 10-243786, WO 00/66744, WO 00/61730). Since PQQGDH exhibits a high oxidation activity for glucose and is a coenzyme-associated enzyme that does not require oxygen as an electron acceptor, it is useful as a recognition element of a glucose sensor.

PQQGDHs catalyze the reaction in which glucose is oxidized to produce gluconolactone. PQQGDHs include membrane-bound enzymes and water-soluble enzymes. Membrane-bound PQQGDHs are single peptide proteins having a molecular weight of about 87 kDa and widely found in various gram-negative bacteria. Water-soluble PQQGDHs have been identified in several strains of *Acinetobacter calcoaceticus* (Biosci. Biotech. Biochem. (1995), 59(8), 1548-1555), and their structural genes were cloned to show the amino acid sequences (Mol. Gen. Genet. (1989), 217:430-436). The water-soluble PQQGDH derived from *A. calcoaceticus* is a homodimer consisting of two subunits having a molecular weight of about 50 kDa. Each subunit has one PQQ molecule and three $Ca^{++}$ cations. The dimer protein has two active centers, while the monomer enzyme does not have a GDH activity. Thus, formation of a dimer structure is essential for the GDH activity. The X-ray analysis of the crystalline structure of the water-soluble PQQGDH revealed the higher-order structure of the enzyme (J. Mol. Biol., 289, 319-333 (1999), A. Oubrie et al., EMBO Journal, 18(19), 5187-5194 (1999), A. Oubrie et al., PNAS, 96(21), 11787-11791 (1999), A. Oubrie et al.).

The object of the present invention is to provide a modified water-soluble PQQGDH having improved thermal stability.

SUMMARY OF THE INVENTION

The present invention provides a water-soluble PQQGDH wherein two subunits are linked together via one or more disulfide bonds.

The term "PQQGDH" as used herein represents a glucose dehydrogenase associated with pyrroloquinoline quinine as a coenzyme. The term "modified PQQGDH" means a PQQGDH in which a part of the structure of the naturally occurring glucose dehydrogenase has been chemically modified. Such a modification can be effected by, for example, substituting at least one amino acid residue of the protein with another naturally occurring or non-naturally occurring amino acid residue, or by deleting or adding one or more amino acids. The amino acid numbering herein starts from the initiator methionine as the +1 position. Thus, the first amino acid residue Asp found in SEQ ID NO: 1 represents the 25th amino acid residue of the PQQGDH of *A. calcoaceticus*.

As used herein, the term "disulfide bond" means an —S—S-bond, and the term "subunit" means each monomer subunit constituting the dimer.

Preferably, in the water-soluble PQQGDH of the invention, at least one amino acid residue other than cysteine of a naturally occurring PQQGDH is substituted with a cysteine residue. Also preferably, the water-soluble PQQGDH of the invention is derived from *Acinetobacter calcoaceticus*. In a particularly preferred embodiment of the PQQGDH of the invention, Ser415 of the amino acid sequence defined by SEQ ID NO: 1 is substituted with a cysteine residue, and a disulfide bond is formed between cysteine residues on each of the two subunits.

In another preferred embodiment, Tyr414 of the amino acid sequence defined by SEQ ID NO: 1 is substituted with a cysteine residue, and a disulfide bond is formed between cysteine residues on each of the two subunits.

In another preferred embodiment, Asp340 and Tyr418 of the amino acid sequence defined by SEQ ID NO: 1 are both substituted with cysteine residues, and a disulfide bond is formed between cysteine residues on each of the two subunits.

In a particularly preferred embodiment of the PQQGDH of the invention, the PQQGDH comprises the sequence:
Pro Thr Tyr Cys Thr Thr Tyr (SEQ ID NO: 3).

In another preferred embodiment, the PQQGDH comprises the sequence:
Pro Thr Cys Cys Thr Thr Tyr (SEQ ID NO: 4).

In another preferred embodiment, the PQQGDH comprises the sequences:
Thr Gly Lys Asn Phe Val Pro (SEQ ID NO: 9) and Ser Thr Thr Tyr Asp Asp Ala (SEQ ID NO: 10).

The present invention also provides a gene encoding the PQQGDH of the invention, a vector containing the gene and a transformant containing the gene, as well as a glucose assay kit and a glucose sensor comprising the PQQGDH of the present invention.

The modified PQQGDHs of the present invention have excellent thermal stability and exhibit high oxidation activity for glucose, so that they are useful for assaying glucose with high sensitivity and high specificity. Particularly, the modified PQQGDHs of the invention are expected to provide the advantages that the enzymes can be produced at high yield with less inactivation during preparation/purification steps; the enzymes can be easily stored in solutions because of their high stability; the enzymes can be used to prepare an assay kit or an enzyme sensor with less inactivation; and the assay kit or enzyme sensor prepared with the enzymes has excellent storage properties because of their high thermal stability.

PREFERRED EMBODIMENTS OF THE INVENTION

Structure of Modified PQQGDHs

In the PQQGDH of the present invention, two subunits are linked together via one or more disulfide bonds in the homodimer structure, whereby exhibiting a great thermal stability. To construct such a linked structure, at least one amino acid residue located in proximity to each other at the interface of each monomer in the dimer structure may be substituted with a cysteine residue and allow a disulfide bond to form between the subunits.

The water-soluble PQQGDH has the amino acid sequence defined by SEQ ID NO: 1, and its higher-order structure has been demonstrated using X-ray analysis of the crystalline structure (J. Mol. Biol., 289, 319-333(1999), EMBO Journal, 18(19), 5187-5194 (1999)). According to the putative higher order-structure, Ser415 residues on the monomers are placed in proximity to each other on the monomer interface when a dimer structure is formed. It has been found that substitution of the Ser415 residues with Cys to allowed a disulfide bond to form between the monomers resulting in a modified enzyme having greater thermal stability than the wild-type enzyme.

This is probably because the formation of a disulfide bond improved the stability of the quaternary structure of the water-soluble PQQGDH dimer. This is consistent with the findings that the dimer structure can be stabilized by cross-linking chemical modification (JP A 2000-262281) or by forming a tether structure (JP A 2001-37483), resulting in improved thermal stability of PQQGDH.

In addition, Asn340 and Tyr418 positioned with facing each other at a short distance on the monomer interface of PQQGDH-B were substituted with Cys residues to allow two disulfide bonds to form between the monomers. A modified enzyme having a considerably greater thermal stability than the wild-type enzyme was obtained.

Based on the teaching of the instant application and the information on the putative hither-order structure of the enzyme, a person skilled in the art can easily recognize the amino acid residues located in proximity to each other on the interface of the monomers in the dimer structure and substitute the amino acid residues with cysteine to obtain a modified glucose dehydrogenase having improved thermal stability. The amino acid residue to be substituted is not necessary to be located in the same position of each monomer. That is, when a first amino acid residue on one monomer and a second amino acid residue on the other monomer are located in proximity to each other on the interface of the two monomers, both the first and second amino acid residues can be substituted with cysteine residues. In this case, two disulfide bonds will be formed. Similarly, a dimer structure having more than two disulfide bonds can be constructed.

In the modified glucose dehydrogenases of the present invention, other amino acid residues may be partially deleted or substituted or other amino acid residues may be added so far as glucose dehydrogenase activity is retained. Various techniques for such deletion, substitution or addition of amino acid residues are known in the art as described in, for example, Sambrook et al., "Molecular Cloning: A Laboratory Manual", Second Edition, 1989, Cold Spring Harbor Laboratory Press, New York. Those skilled in the art can readily test whether or not a glucose dehydrogenase containing such deletion, substitution or addition has a desired glucose dehydrogenase activity according to the teaching herein. For example, it has been reported that the affinity to the glucose substrate can be improved by substituting certain amino acid residues of a water-soluble PQQGDH with other amino acid residues (JP A 2000-31258, JP A 2000-350588).

Those skilled in the art can also predict and analyze a three-dimensional structure of water-soluble PQQGDHs derived from other organisms, and predict amino acid residues located on the interface of the two monomers according to the teaching herein. Those residues can be substituted with cysteine residues to allow a disulfide bond to form between the monomers to obtain a modified glucose dehydrogenase with improved thermal stability. Particularly, those skilled in the art can compare the primary-, secondary- or tertiary-structure of PQQGDHs from various organisms and easily identify an amino acid residue in PQQGDHs corresponding to Ser415 or Tyr414 or a combination of amino acid residues corresponding to the combination of Asp340 and Tyr418 of the water-soluble PQQGDH derived from *Acinetobacter calcoaceticus*. The modified glucose dehydrogenases of the invention can be obtained by substituting such an amino acid residue with Cysteine according to the teaching herein. These modified glucose dehydrogenases are also within the scope of the present invention.

Preparation Method of the Modified PQQGDH

SEQ ID NO: 2 defines the sequence of the gene encoding the wild-type water-soluble PQQGDH derived from *Acinetobacter calcoaceticus*.

Genes encoding modified PQQGDHs of the present invention can be constructed by replacing the nucleotide sequence encoding a certain amino acid residue in the gene of the wild-type water-soluble PQQGDH with the nucleotide sequence encoding cysteine residue. Various techniques for such site-specific nucleotide sequence substitution are known in the art as described in, for example, Sambrook et al., "Molecular Cloning: A Laboratory Manual", Second Edition, 1989, Cold Spring Harbor Laboratory Press, New York. Thus obtained mutant gene is inserted into an expression vector (for example, a plasmid) and transformed into an appropriate host (for example, E. coil). A number of vector/host systems for expressing a foreign protein are known in the art, and various organisms such as bacteria, yeasts or cultured cells are suitably used as a host.

Since the water-soluble PQQGDH is secreted into the periplasmic space when it is expressed in *E. coli*, the enzyme activity can be easily assayed using the intact cells. The transformant is subjected to heat treatment at 60-70° C. for about 30 minutes, the glucose and the dye PMS-DCIP are added. The residual PQQGDH activity can be visually determined to select clones exhibiting a certain level of residual activity after the heat treatment. The nucleotide sequence of the insert is analyzed.

Thus obtained transformed cells expressing modified PQQGDHs are cultured and harvested by centrifugation or other means from the culture medium. The cells are disrupted with a French press or osmotically shocked to release the periplasmic enzyme into the medium. The sample is ultracentrifuged to give a fraction containing water-soluble PQQGDH. Alternatively, the expressed PQQGDH may be secreted into the medium by using an appropriate host/vector system. The resulting water-soluble fraction is purified by ion exchange chromatography, affinity chromatography, HPLC or the like to prepare a modified PQQGDH of the present invention.

Method for Assaying Enzyme Activity

PQQGDHs of the present invention associate with PQQ as a coenzyme catalyze the reaction in which glucose is oxidized to gluconolactone.

The enzyme activity can be assayed by using the color-developing reaction of a redox dye to measure the amount of the reduced PQQ generated by PQQGDH-catalyzed oxidation of glucose. Suitable color-developing reagents include PMS (phenazine methosulfate)-DCIP (2,6-dichlorophenolindophenol), potassium ferricyanide and ferrocene.

Thermal Stability

Thermal stability of the modified PQQGDHs of the present invention can be evaluated by incubating the enzyme of interest at a high temperature (for example, 55° C.), sampling aliquots at regular intervals and assaying the enzyme activity to monitor the decrease in the enzyme activity with time. Typically, thermal stability of an enzyme is expressed as a heat inactivation half-life, i.e. the time required for the enzyme activity to be reduced to 50% ($t_{1/2}$). Alternatively, thermal stability can also be expressed as the residual enzyme activity after heat treatment of the enzyme for a given period (the ratio of the activity after heat treatment to the activity before heat treatment).

Modified PQQGDHs of the present invention are characterized by having higher thermal stability than that of the wild-type PQQGDH. Thus, they have the advantages that the enzymes can be produced at high yield with less inactivation during preparation/purification steps; the enzymes can be easily stored in solutions because of their high stability; the enzymes can be used to prepare an assay kit or an enzyme sensor with less inactivation; and the assay kit or enzyme sensor prepared with the enzymes of the invention has excellent storage properties because of their high thermal stability.

Glucose Assay Kit

The present invention also relates to a glucose assay kit comprising a modified PQQGDH according to the present invention. The glucose assay kit of the present invention comprises a modified PQQGDH according to the present invention in an amount enough for at least one run of assay. In addition to the modified PQQGDH according to the present invention, the kit typically comprises a necessary buffer for the assay, a mediator, standard glucose solutions for preparing a calibration curve and instructions. Modified PQQGDHs according to the present invention can be provided in various forms such as freeze-dried reagents or solutions in appropriate preservative solutions. Modified PQQGDHs according to the present invention are preferably provided in the form of a holoenzyme, though they may also be provided as an apoenzyme and converted into a holoenzyme before use.

Glucose Sensor

The present invention also relates to a glucose sensor using a modified PQQGDH according to the present invention. Suitable electrodes include carbon, gold, and platinum electrodes, on which the enzyme of the present invention is immobilized by using a crosslinking agent; encapsulation in a polymer matrix; coating with a dialysis membrane; using a photo-crosslinkable polymer, an electrically conductive polymer or a redox polymer; fixing the enzyme in a polymer or adsorbing it onto the electrode with an electron mediator such as ferrocene or its derivatives; or any combination thereof. Modified PQQGDHs of the present invention are preferably immobilized in the form of a holoenzyme on an electrode, though they may be immobilized as an apoenzyme and PQQ may be provided as a separate layer or in a solution. Typically, modified PQQGDHs of the present invention are immobilized on a carbon electrode with glutaraldehyde and then treated with an amine-containing reagent to block glutaraldehyde.

Glucose levels can be measured as follows. PQQ, $CaCl_2$ and a mediator are added to a thermostat cell containing a buffer and kept at a constant temperature. Suitable mediators include, for example, potassium ferricyanide and phenazine methosulfate. An electrode on which a modified PQQGDH of the present invention has been immobilized is used as a working electrode in combination with a counter electrode (e.g. a platinum electrode) and a reference electrode (e.g. an Ag/AgCl electrode). After a constant voltage is applied to the carbon electrode to reach a steady current, a glucose-containing sample is added to measure the increase in current. The glucose level in the sample can be calculated from a calibration curve prepared with glucose solutions at standard concentrations.

The disclosures of all the patents and documents cited herein are entirely incorporated herein by reference. The present application claims priority based on the Japanese Patent Applications No. 2001-70413, the entire disclosure of which is hereby incorporated by reference.

EXAMPLES

The following examples further illustrate the present invention without, however, limiting the same thereto.

Example 1

Construction of Genes Encoding Modified PQQGDHs

Figure 1:
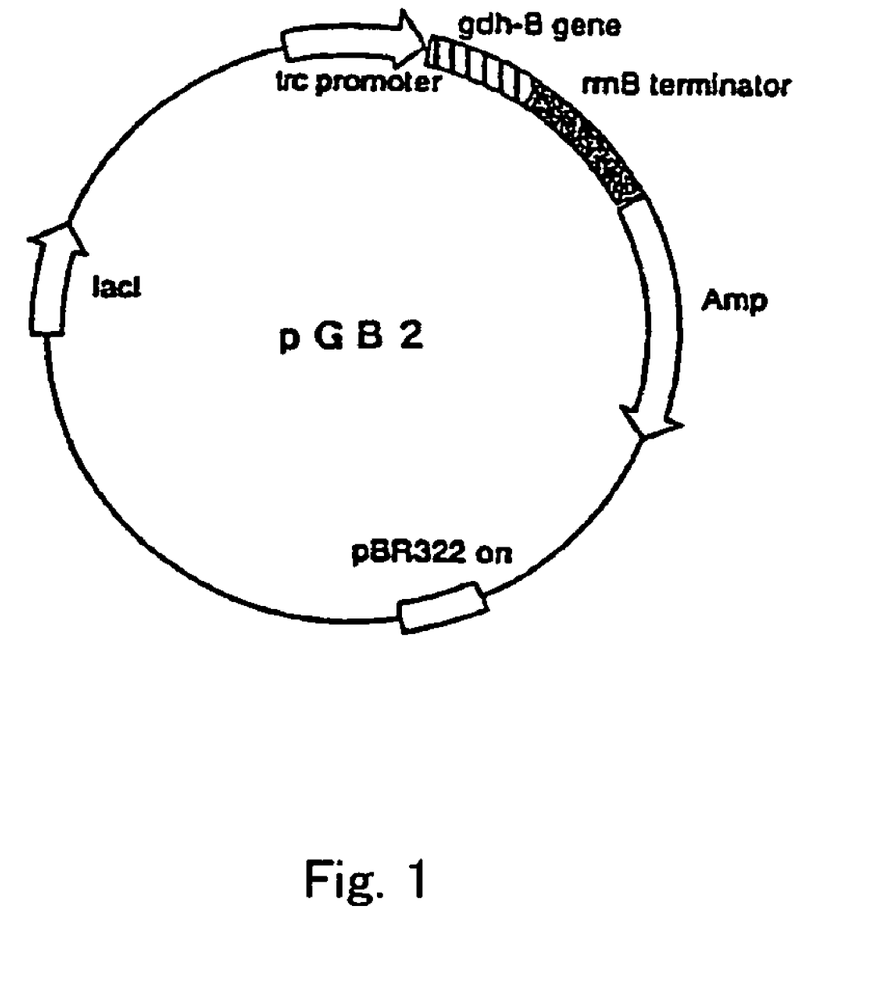
FIG. 1 shows the structure of the plasmid pGB2 used in the present invention.
Figure 2:
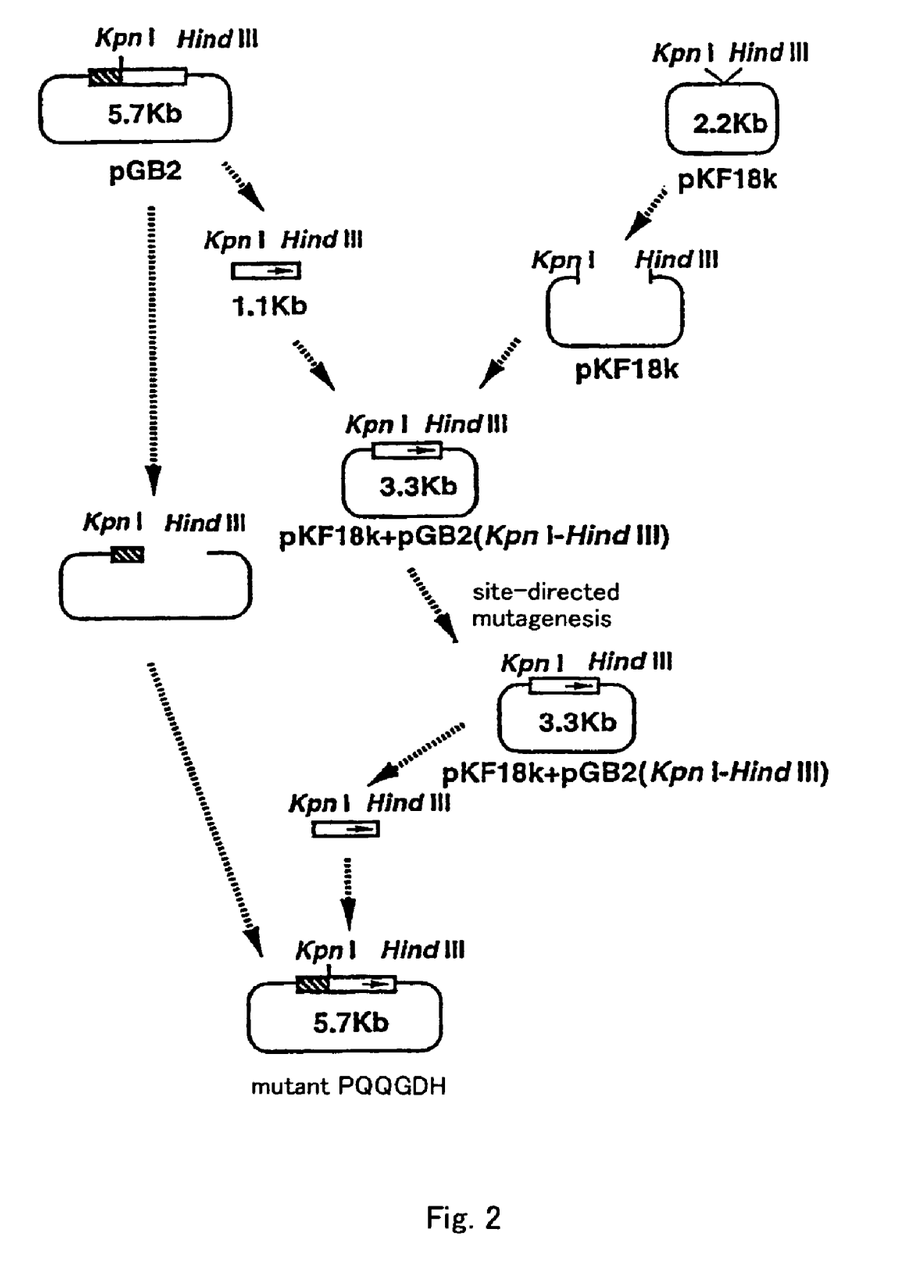
FIG. 2 shows a scheme for preparing a gene encoding a modified enzyme of the present invention.

The amino acid residues were substituted by a point mutation method using the structural gene of the PQQGDH derived from *Acinetobacter calcoaceticus* as defined in SEQ ID NO: 2. Point mutation was made by inserting the structural gene encoding the PQQGDH derived from *Acinetobacter calcoaceticus* into a multicloning site of a vector pTrc99A (Pharmacia) to obtain a plasmid pGB2 (FIG. 1) according to the method shown in FIG. 2.

The sequences of the synthesized oligonucleotide target primers used for the mutagenesis are shown below:
Ser415Cys catcataagtagtgcaataagttggatc
Tyr414Cys/Ser415Cys catcataagtagtgcaacaagttggatctaac
Asp 167Glu aggtgatgatttctcatgctgtga
Ser231Lys cctttggaattttccatcaagatttaagc

```
Ser415Cys          catcataagtagtgcaataagttggatc

Tyr414Cys/         catcataagtagtgcaacaagttggatctaac
Ser415Cys

Asp167Glu          aggtgatgatttctcatgctgtga

Ser231Lys          cctttggaattttccatcaagatttaagc
```

A KpnI-HindIII fragment containing a part of the gene encoding the PQQGDH derived from *Acinetobacter calcoaceticus* was inserted into the vector plasmid pKF18k (Takara Shuzo Co. Ltd.), and used as a template. Fifty fmols of this template, 5 pmol of the selection primer supplied with the Mutan™-Express Km Kit (Takara Shuzo Co., Ltd.) and 50 pmol of the phosphorylated target primer were mixed with the annealing buffer supplied with the kit in an amount equivalent to 1/10 of the total volume (20 μl), and the mixture was heated at 100° C. for 3 minutes to denature the plasmid into a single strand. The selection primer serves for reversion of dual amber mutations on the kanamycin-resistance gene of pKF18k. The mixture was placed on ice for 5 minutes to anneal the primers. To this mixture were added 3 μl of the extension buffer supplied with the kit, 1 μl of T4 DNA ligase, 1 μl of T4 DNA polymerase and 5 μl of sterilized water to synthesize a complementary strand.

The synthetic strand was transformed into a DNA mismatch repair-deficient strain E. coil BMH71-18mutS and shake-cultured overnight to amplify the plasmid.

The plasmid was extracted from the culture and transformed into E. coil MV1184 and then extracted from the cells. These plasmids were sequenced to confirm the introduction of the intended mutations. These fragments were substituted for the KpnI-HindIII fragment of the gene encoding the wild-type PQQGDH on the plasmid pGB2 to construct the genes encoding the modified PQQGDHs. To introduce more than one mutation, the above steps were repeated. Thus, genes encoding the mutations Ser415Cys, Tyr414Cys/Ser415Cys, and Asp167Glu/Ser231Lys/Ser415Cys were obtained.

Example 2

Preparation of Modified Enzymes

The gene encoding the wild-type or each modified PQQGDH was inserted into the multicloning site of an E. coil expression vector pTrc99A (Pharmacia), and the resulting plasmid was transformed into the E. coil strain DH5α. The transformant was shake-cultured at 37° C. overnight in 450 ml of L medium (containing 50 μg/ml of ampicillin and 30 μg/ml of chloramphenicol) in a Sakaguchi flask, and inoculated on 7 L of L medium containing 1 mM $CaCl_2$ and 500 μM PQQ. About 3 hours after starting cultivation, isopropyl thiogalactoside was added at a final concentration of 0.3 mM, and cultivation was further continued for 1.5 hours. The cultured cells were harvested from the medium by centrifugation (5,000×g, 10 min, 4 C), and washed twice with a 0.85% NaCl solution. The collected cells were disrupted with a French press, and centrifuged (10,000×g, 15 min, 4° C.) to remove undisrupted cells. The supernatant was ultracentrifuged (160,500×g (40,000 r.p.m.), 90 min, 4° C.) to give a water-soluble fraction.

Thus obtained water-soluble fraction was dialyzed against 10 mM phosphate buffer, pH 7.0 overnight. The dialyzed sample was adsorbed to a cation chromatographic column TSKgel CM-TOYOPEARL 650M (Tosoh Corp.), which had been equilibrated with 10 mM phosphate buffer, pH 7.0. This column was washed with 750 ml of 10 mM phosphate buffer, pH 7.0, and then the enzyme was eluted with 10 mM phosphate buffer, pH 7.0, containing 0-0.2 M NaCl at a flow rate of 5 ml/min. Fractions having GDH activity were collected and dialyzed against 10 mM MOPS-NAOH buffer, pH 7.0 overnight. Thus, an electrophoretically homogeneous modified PQQGDH protein was obtained. This was used in the subsequent examples as a purified enzyme sample.

Example 3

Disulfide Bond Formation

The modified enzyme Ser415Cys obtained in Example 2 was heat denatured in the absence of mercaptoethanol and analyzed by SDS-PAGE. A main band of 100 kDa and a minor band of 50 kDa was observed, indicating that a disulfide bond was formed between the subunits.

Example 4

Assay of Enzyme Activity

Enzyme activity was assayed by using PMS (phenazine methosulfate)-DCIP (2,6-dichlorophenolindophenol) in 10 mM MOPS-NaOH buffer (pH 7.0) to monitor changes in the absorbance of DCIP at 600 nm with a spectrophotometer. The reaction rate of the enzyme was expressed as the rate of decrease in the absorbance. The enzyme activity for reducing 1 μmol of DCIP in 1 minute was defined to be 1 U. The molar extinction coefficient of DCIP at pH 7.0 was 16.3 $mM^{-1}$.

Example 5

Evaluation of Thermal Stability

Figure 3:
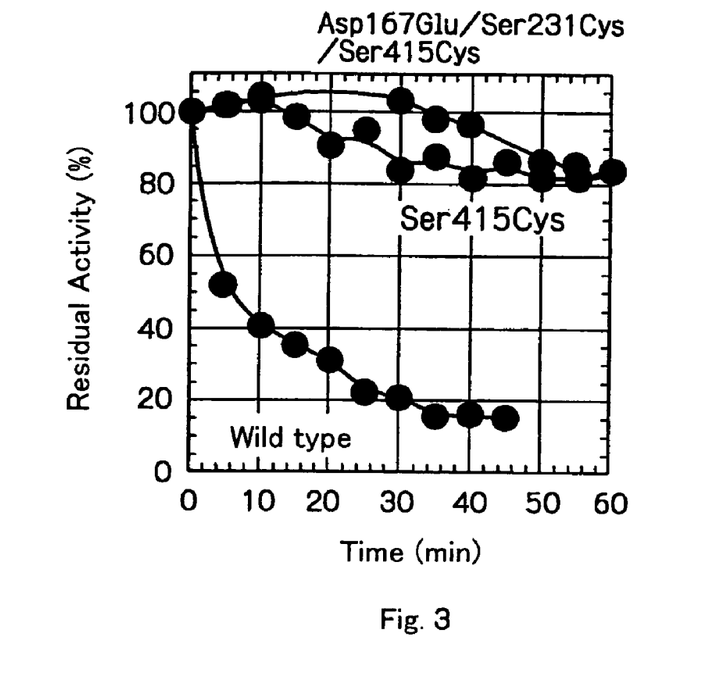
FIG. 3 shows thermal stability of a modified enzyme of the present invention.

Each of the samples of the wild-type and modified PQQGDHs obtained in Example 2 was converted into a holoenzyme in the presence of 1 μM PQQ and 1 mM $CaCl_2$ for 1 hour or longer and then incubated at 55° C. Aliquots were sampled at regular intervals and rapidly cooled on ice. These samples were assayed for the enzyme activity by the method of Example 4. The results are shown in FIG. 3.

Both the modified enzymes Ser415Cys and Asp167Glu/Ser231Lys/Ser415Cys showed much less inactivation at 55° C. than the wild-type enzyme. The modified enzyme Ser415Cys/Tyr414Cys lost its activity by 50% with a heat treatment at 55° C. for 10 minutes, however, the residual activity of 50% was retained for another 50 minutes. The half life, i.e. the time required for losing the 50% of the activity ($t_{1/2}$), of the wild-type purified enzyme and the modified enzymes Ser415Cys and Asp167Glu/Ser231Lys/Ser415Cys were 14 minutes, 183 minutes, and 136 minutes, respectively.

Then, the heat stable properties of the enzymes of the invention were tested. Each of the purified samples of the wild-type enzyme and the modified enzyme Ser415Cys obtained in Example 2 was converted into a holoenzyme in the presence of 1 μM PQQ and 1 mM $CaCl_2$ for 1 hour or longer. Then, each sample was incubated at a given temperature in 10 mM MOPS buffer (pH 7.0) containing 1 μM PQQ and 1 mM $CaCl_2$ for 10 minutes, and then rapidly cooled on ice. These samples were assayed for enzyme activity by the method of Example 4 to determine the residual activity relative to the activity before heat treatment.

Figure 4:
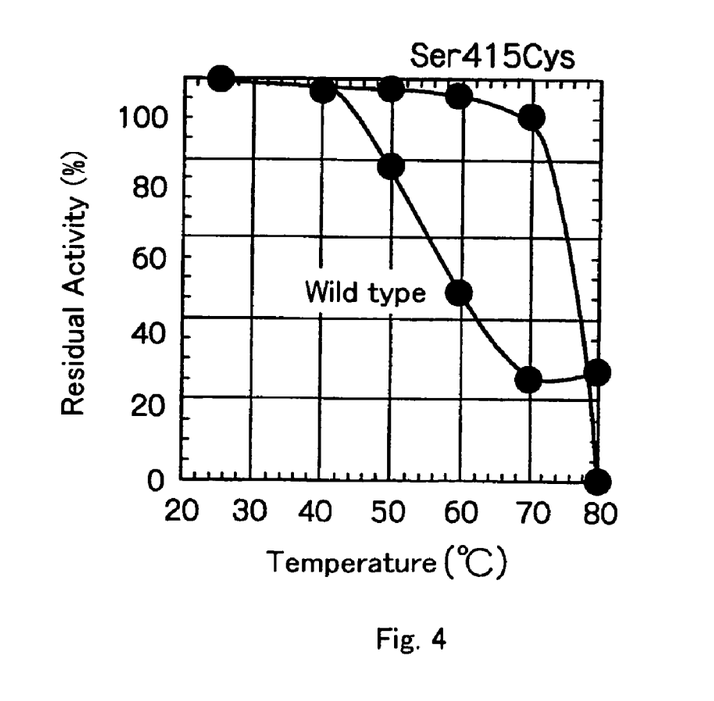
FIG. 4 shows thermal stability of a modified enzyme of the present invention.

The results are shown in FIG. 4. While the wild-type enzyme lost 50% or more of the activity by heat treatment at 60° C., the modified enzyme Ser415Cys showed the residual activity of 90% even at 70° C. Thus, the modified PQQGDH of the present invention was shown to have higher thermal stability than the wild-type PQQGDH.

Example 6

Evaluation of Enzyme Activity

Each of the samples of the wild-type enzyme and the modified enzyme Ser415Cys obtained in Example 2 was converted into a holoenzyme in the presence of 1 µM PQQ and 1 mM CaCl$_2$ for 1 hour or longer. Aliquot of 187 µl was combined with 3 µl of an activating reagent (prepared from 48 µl of 6 mM DCIP, 8 µl of 600 mM PMS and 16 µl of 10 mM phosphate buffer, pH 7.0) and 10 µl of glucose solutions at various concentrations, and assayed for the enzyme activity at room temperature by the method shown in Example 4. The Km and Vmax were determined by plotting the substrate concentration vs. enzyme activity. The modified enzyme Ser415Cys had a Km value for glucose of about 16 mM and kcat value of 3461 sec$^{-1}$. The wild-type PQQGDH had a Km value for glucose of about 27 mM and kcat value of 3436 sec$^{-1}$. These results show that the modified PQQGDH Ser415Cys exhibits high activity comparable to that of the wild-type PQQGDH.

Example 7

Evaluation of Substrate Specificity

The substrate specificity of the wild-type enzyme and the modified enzymes Ser415Cys and Asp167Glu/Ser231Lys/Ser415Cys prepared in Example 2 were tested. The substrates tested were glucose, allose, 3-o-methyl-D-glucose, galactose, lactose and maltose. Each sample was incubated with 20 mM of each substrate for 30 minutes in the presence of 1 µM PQQ and 1 mM CaCl$_2$, and assayed for the enzyme activity in the same manner as Example 4 to determine the relative activity to the activity for glucose. As shown in Table 1, the modified enzymes Ser415Cys of the present invention showed similar substrate specificity to that of the wild-type enzyme. Also the modified enzymes having Ser415Cys and Ser231Lys/Asp 167Glu substitutions exhibit higher substrate specificity for glucose than the wild-type enzyme, probably due to the presence of Asp 167Glu mutation.

TABLE 1

| | wild-type | | Ser415Cys | | Asp167Glu/Ser231 Lys/Ser415Cys | |
|---|---|---|---|---|---|---|
| | Km (mM) | Kcat (s$^{-1}$) | Km (mM) | kcat (s$^{-1}$) | Km(mM) | kcat(s$^{-1}$) |
| glucose | 27 | 3436 | 16 | 3461 | 53 | 1248 |
| allose | 36 | 2509 | 21 | 3664 | 89 | 301 |
| 3-o-methyl-glucose | 29 | 3011 | 26 | 5823 | 127 | 412 |
| galactose | 5 | 232 | 7 | 337 | 165 | 240 |
| lactose | 19 | 1659 | 20 | 2973 | 31 | 507 |
| maltose | 26 | 1930 | 11 | 2477 | 102 | 590 |

Example 8

Glucose Assay

Figure 5:
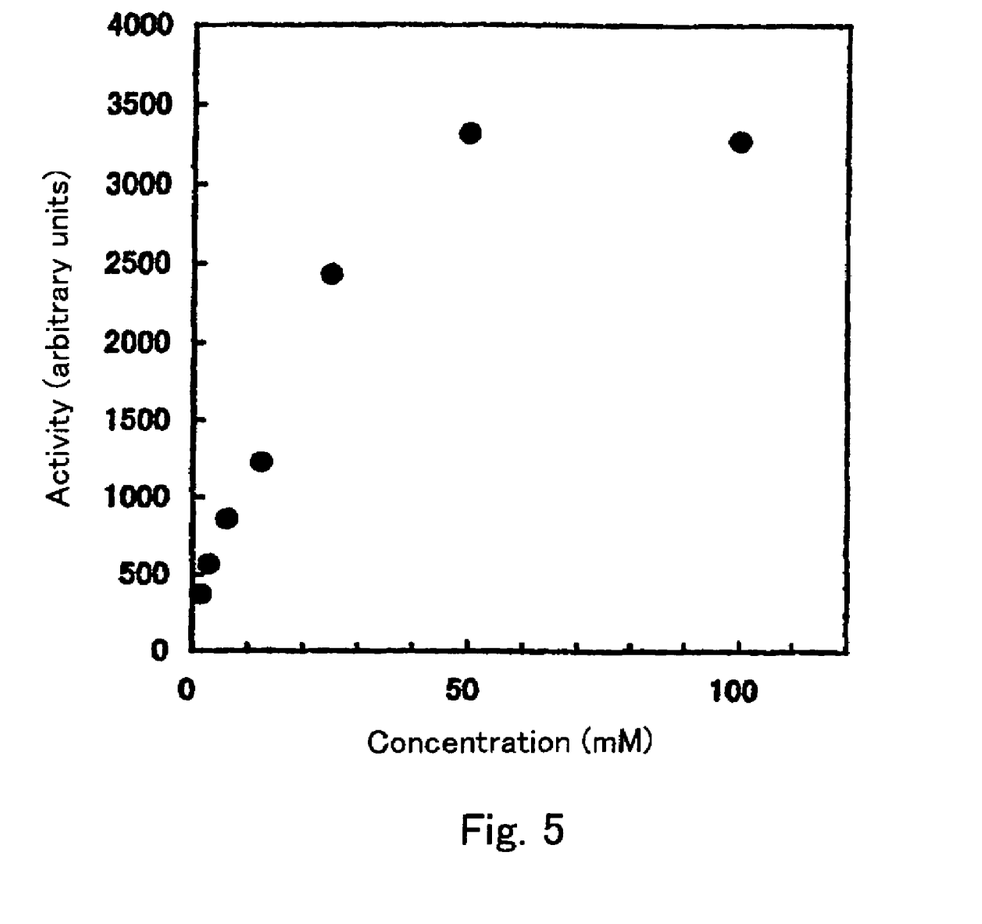
FIG. 5 shows a glucose assay using a modified PQQGDH of the present invention.

A modified PQQGDH was used for assaying glucose. The modified enzyme Ser415Cys was converted into a holoenzyme in the presence of 1 µM PQQ and 1 mM CaCl$_2$ for 1 hour or longer, and assayed for the enzyme activity in the presence of glucose at various concentrations as well as 5 µM PQQ and 10 mM CaCl$_2$ by the method described in Example 4. The assay was based on changes of the absorbance of DCIP at 600 nm. As shown in FIG. 5, the modified PQQGDH Ser415Cys is used for assaying glucose in the range of 5 mM-50 mM.

Example 9

Preparation and Evaluation of Enzyme Sensor

Five units of the modified enzyme Ser415Cys was freeze-dried with 20 mg of carbon paste. After thorough mixing, the mixture was applied only on the surface of a carbon paste electrode preliminarily filled with about 40 mg of carbon paste and polished on a filter paper. This electrode was treated in 10 mM MOPS buffer (pH 7.0) containing 1% glutaraldehyde at room temperature for 30 minutes followed by 10 mM MOPS buffer (pH 7.0) containing 20 mM lysine at room temperature for 20 minutes to block glutaraldehyde. The electrode was equilibrated in 10 mM MOPS buffer (pH 7.0) at room temperature for 1 hour or longer and then stored at 4° C.

Thus prepared enzyme sensor was used to measure glucose levels. The enzyme sensor having a modified PQQGDH of the present invention immobilized thereon is used for assaying glucose in the range of 1 mM-12 mM.

Example 10

Preparation of Modified Enzyme Asn340Cys/Tyr418Cys

The structure of PQQGDH-B was displayed using a molecular modeling and visualizing software Ras Mol based on the report by Oubrie et al. (Oubrie A, et al., (1999) J. Mol. Biol. 289: 5187-5194; Oubrie A, et al., (1999) EMBO J. 18: 5187-5159; Oubrie A, et al., Biochemistry 96: 11787-11791). The residue Asn340 located in the 4CD Loop and the residue Tyr418 located in the 5CD Loop are faced to each other on the dimer interface of PQQGDH-B, and the distance between the side chains of these residues were 4 Å or less. It was expected that a disulfide bond could be formed by substituting each of these amino acid residues with cysteine.

Point mutations corresponding to the Asn340Cys/Tyr418Cys mutation were introduced into the gene encoding PQQGDH according to the method described in Example 1. The primers used were as follows:

Asn340Cys gggacaaagcatttaccagtcc (SEQ ID NO: 11)

Tyr418Cys catcggtacagcgtcatcacaagtagtgc (SEQ ID NO: 12)

```
                                        (SEQ ID NO: 11)
    Asn340Cys      gggacaaagcatttaccagtcc (SEQ ID NO: 12)
    Tyr418Cys      catcggtacagcgtcatcacaagtagtgc
```

Purified enzyme sample of the modified enzyme was prepared according to the method described in Example 2. Non-denature SDS-PAGE analysis revealed a band of about 100 kDa, indicating that a disulfide bond was formed between the subunits.

Example 11

Evaluation of the Activity, Thermal Stability and Substrate Specificity of Modified Enzyme Asn340Cys/Tyr418Cys The enzyme activity of the modified enzyme Asn340Cys/Tyr418Cys prepared in Example 10 was measured as described in Example 4. The activity of the wild-type enzyme was 3347 U/mg, while that of the modified enzyme was 2877 U/mg. The Km value calculated from the activity on various substrate concentrations was 18 mM, which was the same as the wild-type enzyme. The substrates specificity was assayed using various substrates including glucose, lactose, 2-deoxy glucose, maltose, allose, 3-o-methyl-D-glucose, galactose, xylose and mannose. The substrate specificity pattern of the modified enzyme was the same as the wild-type enzyme.

Figure 6:
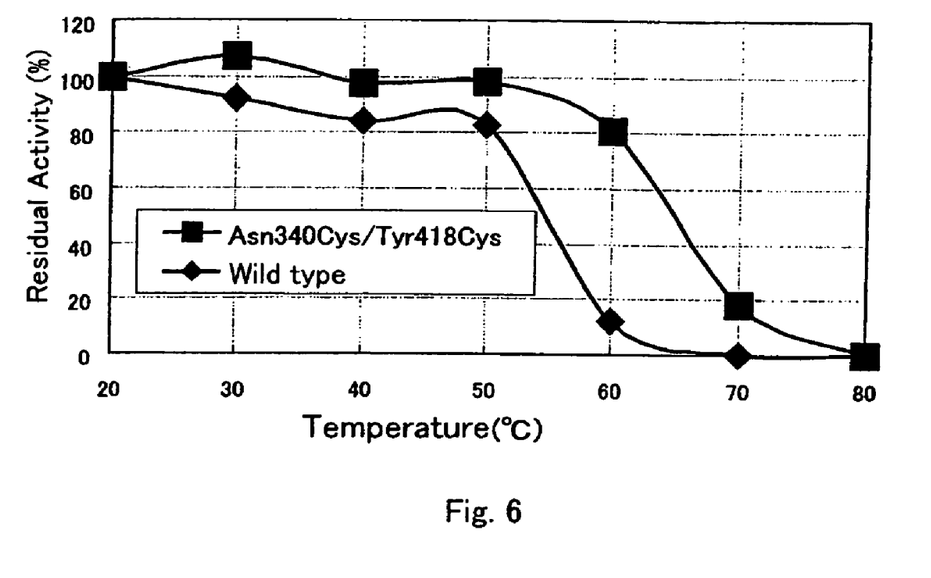
FIG. 6 shows thermal stability of a modified enzyme of the present invention.

To test the thermal stability, the purified enzyme sample was heat treated at the constant temperature of 55° C. for 0, 5, 10, 20, 45, 60, 90, 120, 150, or 180 minutes, and change in the activity was measured. The wild-type enzyme was heat treated for 60 minutes or less. The results are shown in FIG. 6. The activity retained after the heat treatment for given period of time is expressed as a relative activity compared to the activity before the heat treatment. As shown in FIG. 6, the wild-type enzyme appeared to have a half life of 10 minutes or less, and completely lost the activity within 60 minutes. The modified enzyme Asn340Cys/Tyr418Cys showed a half life of more than 60 minutes, and it even showed a residual activity of 20% after 180 minutes incubation. To calculate the half life of the enzyme, natural logarithm of the specific activity was plotted with respect to the incubation time to obtain the time required for the residual activity to reach 50%. The half life of the wild-type enzyme was about 10 minutes, while that of the modified enzyme Asn340Cys/Tyr418Cys was 70 minutes.

Figure 7:
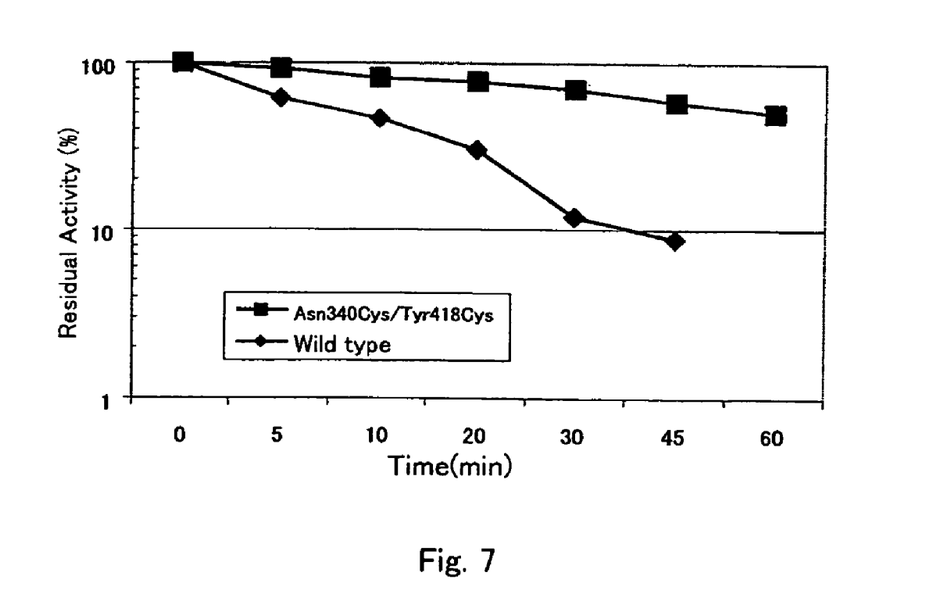
FIG. 7 shows thermal stability of a modified enzyme of the present invention.

Next, the residual activity after heat treatment for 10 minutes at various temperatures from 20 to 80° C. was measured. The results are shown in FIG. 7. The residual activity is expressed as a relative activity compared to the activity at 20° C. The wild-type enzyme lost its activity at 50-60° C. The residual activity at 50° C., 60° C. and 70° C. were 80%, 10% and 0% respectively. In contrast, the modified enzyme Asn340Cys/Tyr418Cys showed its residual activity of about 100% at 50° C., and 80% at 60° C. It even retains the residual activity of 20% at 70° C. where the wild-type enzyme completely lost its activity.

Accordingly, the modified enzyme Asn340Cys/Tyr418Cys had a greater thermal stability than the wild-type enzyme.

INDUSTRIAL APPLICABILITY

The modified water-soluble PQQGDH of the invention is useful as an assay devise of glucose sensors.

---

The invention claimed:

1. An isolated mutant water-soluble pyrrolo-quinoline quinine glucose dehydrogenase (PQQGDH) protein, wherein two subunits of said mutant PQQGDH are linked together via one or more disulfide bonds, wherein said mutant PQQGDH is a mutant of a PQQGDH comprising the amino acid sequence of SEQ ID NO:1 and wherein said mutant PQQGDH only has one or more amino acid substitutions selected from the group consisting of:
   (1) serine at position 415 is substituted with a cysteine residue in SEQ ID NO:1,
   (2) tyrosine at position 414 is substituted with a cysteine residue in SEQ ID NO:1,
   (3) aspartate at position 340 is substituted with a cysteine residue in SEQ ID NO:1, and
   (4) tyrosine at position 418 is substituted with a cysteine residue in SEQ ID NO:1.

2. The mutant PQQGDH of claim 1 wherein serine at position 415 of the amino acid sequence of SEQ ID NO: 1 is substituted with a cysteine residue.

3. The mutant PQQGDH of claim 1 wherein tyrosine at position 414 of the amino acid sequence of SEQ ID NO: 1 is substituted with a cysteine residue.

4. The mutant PQQGDH of claim 1 wherein tyrosine at position 414 and serine at position 415 of the amino acid sequence of SEQ ID NO: 1 are both substituted with cysteine residues.

5. The mutant PQQGDH of claim 1 wherein aspartate at position 340 and tyrosine at position 418 of the amino acid sequence of SEQ ID NO: 1 are both substituted with cysteine residues.

6. A glucose assay kit comprising the mutant PQQGDH of claim 1.

7. A glucose sensor comprising the mutant PQQGDH of claim 1.

8. An isolated mutant PQQGDH protein, wherein two subunits of said mutant PQQGDH are linked together via one or more disulfide bonds, wherein said mutant PQQGDH is a mutant of a PQQGDH comprising the amino acid sequence of SEQ ID NO:1 and wherein said mutant PQQGDH only has the following amino acid substitutions:
   (1) serine at position 415 is substituted with a cysteine residue and aspartate at position 167 is substituted with a glutamate residue in SEQ ID NO:1,
   (2) serine at position 415 is substituted with a cysteine residue and serine at position 231 is substituted with a lysine residue in SEQ ID NO:1, or
   (3) serine at position 415 is substituted with a cysteine residue, aspartate at position 167 is substituted with a glutamate residue and serine at position 231 is substituted with a lysine residue in SEQ ID NO:1.

* * * * *